United States Patent [19]

Verhoeven et al.

[11] Patent Number: 5,350,800
[45] Date of Patent: Sep. 27, 1994

[54] METHOD FOR IMPROVING THE BIOCOMPATIBILITY OF SOLID SURFACES

[75] Inventors: Michel Verhoeven, Maastricht; Patrick Cahalan; Linda Cahalan, both of Schepersgats; Marc Hendriks, Baunssum; Benedicte Foache, Maastricht, all of Netherlands

[73] Assignee: Medtronic, Inc., Minneapolis, Minn.

[21] Appl. No.: 5,711

[22] Filed: Jan. 19, 1993

[51] Int. Cl.$^5$ ............... A61F 2/54; A61F 2/02; A61K 9/22
[52] U.S. Cl. ............... 525/54.2; 523/112; 604/266; 424/409; 424/422
[58] Field of Search ............... 525/54.2; 523/112; 604/266; 424/409, 422

[56] References Cited

U.S. PATENT DOCUMENTS

| | | | |
|---|---|---|---|
| 3,826,678 | 7/1974 | Hoffman | 424/423 |
| 4,521,564 | 6/1985 | Solomon | 525/54.1 |
| 4,565,740 | 1/1986 | Golander | 428/409 |
| 5,053,048 | 10/1991 | Pinchuk | 623/1 |
| 5,055,316 | 10/1991 | Hoffman | 427/2 |
| 5,080,924 | 1/1992 | Kamel | 427/2 |
| 5,132,108 | 7/1992 | Narayanan | 424/78.17 |
| 5,167,960 | 12/1992 | Ito et al. | 604/266 |
| 5,217,492 | 6/1993 | Guire et al. | 604/266 |
| 5,263,992 | 11/1993 | Guire | 604/266 |

OTHER PUBLICATIONS

"Adhesion of Endothelial Cells and Adsorption of Serum Proteins on Gas Plasma-Treated Polytetrafluoroethylene" Dekker et al., Biomaterials, 1991, vol. 12 Mar.

"Preparation of Three Types of Heparin-Sepharose and Their Binding Activities to Thrombin and Antithrombin III", by Funahashi, et al., Analytical Biochemistry 126,414-126,421 (1982).

"Materials for Enhancing Cell Adhesion by Immobilization of Cell-Adhesive Peptide", by Ito et al. in Journal of Biomedical Materials Research, vol. 25, 1325-1337 (1991).

Primary Examiner—Nathan M. Nutter
Attorney, Agent, or Firm—Daniel W. Latham; Harold R. Patton

[57] ABSTRACT

A method for attaching a biomolecule having a plurality of carboxyl groups to an aminated solid surface by reacting the biomolecule with a carbodiimide to effect an activation of the carboxyl groups of the biomolecule, reacting the carbodiimide activated biomolecule with the solid surface to covalently bind the biomolecule to the aminated solid surface, and then selectively restoring carboxyl groups to the biomolecule. The selective restoration of carboxyl groups can be carried out by mild hydrolysis and restores the functionality of the biomolecule. The method is "selective" since the bonds between the biomolecule and the aminated solid surface remain intact.

10 Claims, No Drawings

METHOD FOR IMPROVING THE BIOCOMPATIBILITY OF SOLID SURFACES

BACKGROUND OF THE INVENTION

This invention relates to the enhancement of the biocompatibility of various surfaces by binding biomolecules containing carboxyl groups to aminated surfaces.

Medical devices which serve as substitute blood vessels, synthetic and intraocular lenses, electrodes, catheters and the like in and on the body or as extracorporeal devices intended to be connected to the body to assist in surgery or dialysis are well known. However, the use of such biomaterials in medical devices can stimulate adverse body responses, including rapid thrombogenic action. Various plasma proteins play a role in initiating platelet and fibrin deposition on plastic surfaces. These actions lead to vascular constriction to hinder blood flow, and the inflammatory reaction that follows can lead to the loss of function of the medical device.

A "biomaterial" may be defined as a material that is substantially insoluble in body fluids and that is designed and constructed to be placed in or onto the body or to contact fluid of the body. Ideally, a biomaterial will not induce undesirable reactions in the body such as blood clotting, tissue death, tumor formation, allergic reaction, foreign body reaction (rejection) or inflammatory reaction; will have the physical properties such as strength, elasticity, permeability and flexibility required to function for the intended purpose; can be purified, fabricated and sterilized easily; will substantially maintain its physical properties and function during the time that it remains implanted in or in contact with the body As used herein, the solid surface of a biomaterial is characterized as "biocompatible" if it is capable of functioning or existing in contact with biological fluid and/or tissue of a living organism with a net beneficial effect on the living organism. Long term biocompatibility is desired for the purpose of reducing disturbance of the host organism. One approach to improved biocompatibility for biomaterials is to attach various "biomolecules" such as growth factors, antimicrobial agents, antithrombogenic agents, and cell attachment proteins to the surface of the material.

A number of approaches have been suggested to attach such biomolecules. One such approach is set forth in U.S. Pat. No. 4,521,564 to Solomon et al. in which an antithrombogenic agent is bonded to a solid polyurethane polymer support. A polymeric amine such as polyvinyl amine, or a polyalkyleneamine is first covalently bonded to the polyurethane substrate to provide an aminated surface. Then, an antithrombogenic agent is covalently bonded to the aminated substrate. The antithrombogenic agent is covalently bonded by first activating the antithrombogenic agent with a carbodiimide and then reacting it with the aminated surface of the substrate material. However, in Funahashi et al. "Preparation of Three Types of Heparin-Sepharose and Their Binding Activities to Thrombin and Antithrombin III" Analytical Biochemistry 126, 414–421 (1982), it was noted that by using the carbodiimide to bind an antithrombogenic agent (e.g. heparin) for an affinity chromatography support, that the carboxyl groups which provide the biomolecule with much of its bioactivity had reacted with the carbodiimide, thereby substantially reducing antithrombin III uptake.

It is therefore an object of the present invention to provide a biocompatible surface having active, covalently bonded biomolecules thereon.

It is also an object of the present invention to covalently attach biomolecules having carboxyl groups to aminated surfaces while retaining their bioactivity.

It is also an object of the present invention to preserve the bioactivity of biomolecules attached by the use of a carbodiimide.

SUMMARY OF THE INVENTION

We have discovered a method for attaching a biomolecule having a plurality of carboxyl groups to an aminated solid surface by reacting the biomolecule with a carbodiimide to effect an activation of the carboxyl groups of the biomolecule, reacting the carbodiimide activated biomolecule with the solid surface to covalently bind the biomolecule to the aminated solid surface, and then selectively restoring carboxyl groups to the biomolecule. The restoration of carboxyl groups can be accomplished by mild hydrolysis. While not wishing to be bound by theory, mild hydrolysis is believed to remove N-acyl urea groups formed as a side product from the reaction between biomolecule and carbodiimide from the functional carboxyl groups on the covalently bound biomolecule thereby restoring much of the functionality of the biomolecule without decoupling the biomolecule from the aminated solid surface.

This method can be used on aminated solid surfaces such as a polymeric substrate having amine functional groups grafted to it, for example, a substrate having a grafted amine functionalized acrylamide-containing polymer or a substrate having attached amine-terminated spacer molecules. The biomolecule can be any biomolecule having a plurality of carboxyl functional groups, and preferably one which is capable of providing a nonthrombogenic, blood-compatible surface such as heparin, streptokinase, tissue plasminogen activator (TPA) or urokinase or cell attachment proteins such as fibronectin or laminin. The carbodiimide used is preferably a water soluble carbodiimide of the structure $R_1N=C=NR_2$ where $R_1$ can be an alkyl or cycloalkyl group and $R_2$ can be an alkylamine or cycloalkylamine group such as 1-ethyl-3-(3-dimethyl-aminopropyl) carbodiimide hydrochloride, or 1-cyclohexyl-3-(2-morpholinoethyl) carbodiimide.

The selective restoration of carboxyl groups can be carried out by mild hydrolysis by incubating the surface and biomolecule in the presence of water at a mild pH for a period of time effective to restore the carboxyl groups. Preferably, the reaction is carried out at a pH in the range of about 8 to 11, at a temperature in the range of about 0° C. to 70° C. and for a period of time in the range of about 1 to 24 hours. For example, the surface with bonded biomolecule can be immersed in an aqueous 1 M solution of sodium bicarbonate (pH=8.2) and heated to about 60° C. for 3 hours. This process is "selective" since the bonds between the biomolecule and the aminated solid surface remain intact.

DETAILED DESCRIPTION OF THE INVENTION

The solid surface that is rendered biocompatible in accordance with the invention desirably is of a synthetic or natural material that is insoluble in physiological fluids and which contains primary or secondary amine groups. The surface may be one or more surfaces of devices intended to function in contact with tissue and/or fluids of living organisms. The substrate for this aminated solid surface of the device may be any suitable metal such as polished titanium or stainless steel or a polymer such as polyurethane, polyvinylpyrrolidone, silicone elastomers, polyolefins such as polyethylene and polypropylene, polytetrafluoroethylene, polyvinyl chloride, polyesters, fluoropolymers, polyacrylates (including polymethacrylates); minerals or ceramics such as hydroxyapatite; human or animal tissue such as bone, skin and teeth; organic materials such as wood, cellulose and compressed carbon; and other natural and synthetic materials such as glass, rubber, wood and the like. Examples of devices which may be provided with biocompatible surfaces in accordance with this invention include vascular graft tubing, dialysis tubing or membrane, blood oxygenator tubing or membrane, ultrafiltration membrane, intra aorticballoon, blood bag, catheter, suture, soft or hard tissue prosthesis, synthetic prosthesis, artificial organs, and lenses for the eye such as contact and intraocular lenses. While not wishing to be bound by theory, mild hydrolysis is believed to remove N-acyl urea groups from the functional carboxyl groups on the covalently bound biomolecule thereby restoring the functionality of the biomolecule without decoupling the biomolecule from the aminated solid surface.

If the substrate material does not have primary or secondary amines at its surface, such amine groups can be added to the surface by grafting or adsorbing an amine-containing chemical moiety onto the substrate material. Grafting could be accomplished by covalent or ionic attachment. For example, polyvinyl amines or polyalkylimines can be covalently attached to polyurethane according to the method taught by U.S. Pat. No. 4,521,564 to Solomon et al. the disclosure of which is incorporated herein by reference. Or, for example, an aminosilane can be attached to the surface as set forth in U.S. Pat. No. 5,053,048 to Pinchuk the disclosure of which is also incorporated herein by reference. Or, for example, a grafted acrylamide-containing polymer can be attached by radiation grafting (followed by amine functionalization) as set forth in U.S. Pat. No. 3,826,678 to Hoffman et al. the disclosure of which is also incorporated herein by reference. A substrate having attached amine-terminated spacer molecules is preferred.

A spacer molecule is a molecule or compound which is capable of attachment to a solid surface, is large enough to extend from the surface of said surface and is capable of immobilizing a biomolecule and/or biomolecules. The spacer insures that the active site of the biomolecule is held outward away from the support so as to contact the body fluid efficiently. The spacers are derived from organic molecules having at least two reactive functional groups generally situated at opposing ends of the molecule. Such groups serve as attachment vehicles capable of coupling the spacer to the solid surface and to the biomolecule. The reactive functional groups on the spacer may be the same or different however, they will provide amine functional groups along the solid surface which are available to form covalent bonds with the carboxyl functional groups extending from the biomolecule. Any known method for carrying out coupling reactions between the substrate material and the spacer molecule will suffice. Suitable examples of spacers which may be used in the present invention include, for example, C2 to C12 diamines, (e.g., 1,6-diaminohexane), ethylenediamine tetraacetic acid, 6-aminocaproic acid, aminopropyltriethoxy-silane and homocysteine thiolactone. Polypeptides and proteins may also be used as spacers in the present invention and multiple coupling agents may be used on the same surface if desired.

The biomolecule can be any biomolecule having a plurality of carboxyl groups and, according to the present invention are attached to the surfaces of biomaterials to improve biocompatibility of the biomaterial. The biomolecule may be a growth factor such as endothelial cell growth factor, epithelial cell growth factor, osteoblast growth factor, fibroblast growth factor, platelet derived growth factor, neural growth factor, or angiogenin growth factor; an antimicrobial agent such as lysozyme or penicillin; an antithrombogenic agent such as heparin, fractionated heparins (e.g., on an AT-III column), heparan, heparan sulfate, chondroitin sulfate, modified dextran, albumin, streptokinase, tissue plasminogen activator (TPA) or urokinase; cell attachment proteins such as fibroectin or laminin; a thrombogenic agent such as collagen or a hydrophilic polymer such as hyaluronic acid, chitosan or methyl cellulose, and other proteins, carbonhydrates and fatty acids.

The carbodiimide used is preferably a water soluble carbodiimide of the structure $R_1N=C=NR_2$ where $R_1$ can be an alkyl or cycloalkyl group and $R_2$ can be an alkylamine or cycloalkylamine group such as 1-ethyl-3-(3-dimethyl-aminopropyl) carbodiimide hydrochloride, or 1-cyclohexyl-3-(2-morpholinoethyl) carbodiimide. In the reaction bonding the biomolecule to the animated solid surface, the first step is the reaction between a carboxyl group on the biomolecule and a carbodiimide molecule to form an O-asylisourea ester. This can be carried out in aqueous solution and can be illustrated as follows:

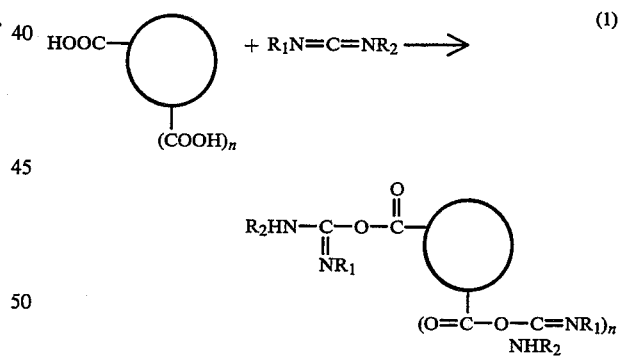

(1)

This reaction is preferably undertaken in a cold solution (0–4° C.) at a pH of about 5 although a room temperature reaction is also acceptable. The biomolecule can be pretreated with carbodiimide and then be brought into contact with the aminated support or the carbodiimide, biomolecule and aminated support can react concomitantly. In the process, the carbodiimide reacts with the carboxyl groups of the biomolecule (1) forming labile O-acylisourea esters (2), susceptible to nucleophilic substitution. Reaction with an amine leads to the formation of a suitable amide bond (2), resulting in effective immobilization of the biomolecule. Part of the remaining activated ester groups will undergo hydrolysis while the remaining ones will undergo an intramolecular rearrangement into relatively stable N-acyl urea groups, blocking the original carboxyl group and impairing bioactivity (3).

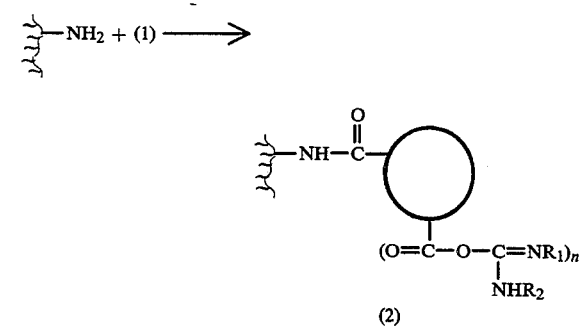

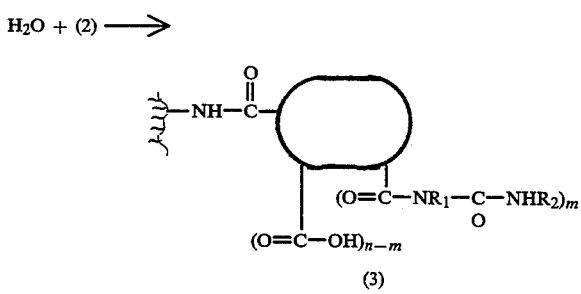

The selective restoration of carboxyl groups by mild hydrolysis can be carried out by incubating the surface and biomolecule in the presence of a buffer for a period of time effective to restore the carboxyl groups. Preferably, the reaction is carried out at a pH in the range of about 8 to 11, at a temperature in the range of about 0° C. to 70° C. and for a period of time in the range of about 1 to 24 hours. For example, the surface with bonded biomolecule can be immersed in an aqueous 1 M solution of sodium bicarbonate (pH=8.2) and heated to about 60° C. for 3 hours. This process is "selective" for restoration of carboxyl group functionality since the bonds made from the carboxyl groups between the biomolecule and the aminated solid surface remain intact. This reaction is as follows:

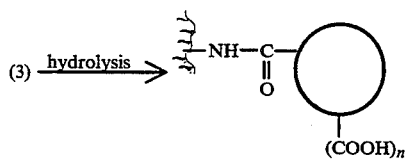

The following examples provide specific embodiments of the invention.

EXAMPLE 1

Polyurethane samples were provided with a grafted acrylamide surface. The samples were corona treated using a Sherman Treaters corona machine type HT3 with an input voltage of 650 volts and an output voltage of 13 KV. Sheet materials were given 6 to 12 passes at 0.25 KW with an electrode distance of 5 mm for each side. The treated sheets were placed in a 40 weight % solution of acrylamide, with stirring, to which 1.75 ml. of aceric ion solution (made by mixing 13.7 grams of ceric ammonium nitrate and 15.75 grams of fuming nitric acid with water to an aqueous solution volume of 250 ml.) was added per 100 grams of acrylamide solution. The test samples were then allowed to react with the monomer solution for one hour at room temperature. The test samples were then removed from the monomer solution and thoroughly rinsed with deionized water.

The test samples were then incubated in water overnight at 60° C. to remove loosely bound polymer chains. The samples were then immersed in a 0.2 M carbonate buffer pH=10.5 at 60° C. to introduce carboxylic acid groups in the grafted gel. Subsequently, ethylene diamine was coupled to these groups by incubating the samples in a buffer solution containing 0.5 M ethylene diamine•2HCl and 0.5 M 4-morphyleneethanesulfonic acid, brought to pH=5.0. Water soluble carbodiimide was added up to a concentration of 0.1 M and amination was conducted for 1-hour at room temperature. Test samples were then thoroughly rinsed in 0.2 M acetate buffer pH=4.6, 1 M NaCl and copious amounts of water.

EXAMPLE 2

Aminated polyurethane samples made substantially as set forth in Example 1 were provided with covalently attached heparin by carbodiimide attachment. Covalent attachment was comparatively tested at both room temperatures and under cold conditions (ice bath). The test samples were immersed in a solution of 5 mg heparin (from porcine intestinal mucosa) per ml of buffer solution (0.5 M 4-morpholineethanesulfonic acid pH=5.0). Water soluble carbodiimide (1-(3-dimethylaminopropyl)-3-ethylcarbodiimide hydrochloride was added to a concentration of 0.01 M. Test samples were stirred in the solution and reacted for 6 hours. The solution was then decanted and the samples were thoroughly rinsed with deionized water, 1 M NaCl, 1 M NaHCO3, and, again, deionized water. One group of test samples was immersed in 1 M NaHCO3 for 3 hours at 60° C. followed by extensive rinsing with deionized water. All samples were then stored in 0.2 M phosphate (pH=6.8) until bioactivity testing. Bioactivity testing was then conducted by determining the extent to which thrombin was deactivated by contact with the surface after incubation of the surface with antithrombin III. Results are shown in Table 1 and expressed in amounts of thrombin activated per unit of surface.

TABLE 1

| Sample | Bioactivity (NIH units thrombin/cm$^2$) |
| --- | --- |
| No hydrolysis, RT reaction | 0.40 |
| No hydrolysis, Cold reaction | 0.48 |
| Hydrolysis, RT reaction | 0.935 |
| Hydrolysis, Cold reaction | 1.126 |

EXAMPLE 3

Fibronectin was attached to an acrylamide-grafted substrate according to the present invention according to the following method.

A hydrolyzed acrylamid-grafted test sample is inserted into a 0.5 M M morpholineethanesulfonic acid (MES) buffered solution of 0.5 M ethylene diamine pH=5.0. To this solution, 1-(3-dimethylaminopropyl)-3-ethylcarbodiimide (EDC) is added until a final concentration of 0.005 M is achieved. The reaction is allowed to proceed for ½ hour at room temperature while stirring. After a short rinse of the sample in deionized water, it is immersed in a 0.5 wt % ghtaraldehyde/0.1

M borate solution, pH=9.0, for ½ hour at room temperature while stirring. Subsequently, the sample is rinsed thoroughly in deionized water, followed by placing the sample in a 1 wt % polyethyleneimine/0.1 M borate solution (pH=9.0) for ¼ hour at room temperature while stirring. The amine-functionalization of the sample is followed by a treatment in 0.2 M acetate buffered solution, pH=4.6, containing 0.1 M sodium cyanoborohydride to stabilize the surface by reduction of imine linkages and any free aldehyde groups.

Fibronectin is then immobilized onto the amine-functionalized substrate surface by reacting the fibronectin molecule with a carbodiimide to effect an activation of the carboxyl groups of the fibronectin molecule and reacting the carbodiimide-activated fibronectin molecule with the amine-functionalized substrate surface. The amine-functionalized substrate is inserted into a 0.5 M MES buffered solution, pH=5.0, containing 0.22 mg/ml lyophilisate (4.556 wt % fibronectin) and EDC is added to this solution until a final concentration of 0.1 M is achieved. The reaction is performed at 0–4° C. for 3 hours while stirring. The test sample is then copiously rinsed with deionized water, 1 M NaCl, 1 M NaHCO$_3$, and again deionized water. The restoration of carboxyl groups can then be accomplished by mild hydrolysis. The sample with fibronectin molecules is incubated in a 1 M NaHCO$_3$ solution, pH=8.2, for 8 hours at 37° C.

EXAMPLE 4

Fibronectin was attached to an acrylamide-grafted substrate according to the present invention using the following method.

A hydrolyzed acrylamide-grafted test sample is inserted into a 0.1 wt % polyethyleneimine solution with the pH adjusted to pH=4. To this solution, 1-(3-dimethylaminopropyl)-3-ethylcarbodiimide is added until a final concentration of 0.01 M is achieved. The reaction is allowed to continue for ½ hour at room temperature while stirring. Fibronectin is then immobilized onto the test sample as set forth in Example 3.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

We claim:

1. A method for improving the bioactivity of a biomaterial in contact with a body or body fluid comprising the steps of:

attaching a biomolecule having a plurality of carboxyl groups thereon, at least some of which impart bioactivity to the biomolecule, to a solid biomaterial surface having primary amine groups thereon by a method comprising the steps of:

(a) reacting the plurality of carboxyl groups of the biomolecule with a carbodiimide to effect an activation of the plurality of carboxyl groups;

(b) reacting at least one of said carbodiimide activated carboxyl groups with the solid biomaterial surface to covalently bind the biomolecule to the solid biomaterial surface by bonding to an amine group thereon;

(c) producing, as a side product of the reactions of steps (a) and (b), groups attached to the carboxyl groups which impart bioactivity to the biomolecule, said attached groups blocking the carboxyl groups and thereby causing reduced bioactivity for the biomolecule;

(d) applying a mild hydrolysis treatment to the covalently bound biomolecule of step (b) at a pH in the range of about 8 to 11 for at least one hour to remove the attached groups of step (c) from the biomolecule while preserving the covalent bond of step (b); and placing the solid biomaterial surface with biomolecule attached according to steps (a)–(d) into contact with the body or body fluid.

2. The method of claim 1 wherein the solid biomaterial surface comprises a polymer having functional primary amine groups grafted to a solid substrate.

3. The method of claim 2 wherein the grafted polymer is an acrylamide polymer functionalized with amine groups.

4. The method of claim 2 wherein the solid substrate is a polymeric substrate selected from the group consisting of polyurethane, silicone elastomer, polyolefins, fluoropolymers, polyesters, and polyacrylates.

5. The method of claim 1 wherein the biomolecule is selected from the group consisting of growth factors, antimicrobial agents, antithrombogenic agents, and cell attachment proteins.

6. The method of claim 5 wherein the biomolecule is heparin.

7. The method of claim 5 wherein the biomolecule is fibronectin.

8. The method of claim 1 wherein the carbodiimide has the structure $R_1N=C=NR_2$ where $R_1$ is an alkyl or cycloalkyl group and $R_2$ is an alkylamine or cyloalkylamine group.

9. The method of claim 8 wherein the carbodiimide is 1-(3-dimethylaminopropyl)-3-ethylcarbodiimide hydrochloride.

10. The method of claim 1 wherein the mild hydrolysis is carried out at a temperature in the range of about 0° C. to 70° C.

* * * * *